United States Patent
Hammond et al.

(10) Patent No.: US 6,201,026 B1
(45) Date of Patent: Mar. 13, 2001

(54) VOLATILE ALDEHYDES AS PEST CONTROL AGENTS

(75) Inventors: David G. Hammond, Berkeley; Isao Kubo, Moraga, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/264,780

(22) Filed: Mar. 9, 1999

(51) Int. Cl.[7] .............................. A01N 35/00; A61L 9/04
(52) U.S. Cl. .................... 514/693; 514/703; 514/705; 424/45
(58) Field of Search .................... 514/693, 703, 514/705; 424/405, 45

(56) References Cited

PUBLICATIONS

Ferguson et al, The Toxicity of Vapours To The Grain Weevil, Annals of Applied Biology, vol. 35, pp. 532–550, 1948.*

Y. Aharoni and J.K. Stewart, *J. Amer. Soc. Hort. Sci.* (1980) 105(6): 926–929, Thrips Mortality.

Y. Aharoni et al., *Journal of Economic Entomology* (1979) 72(4): 493495, Acetaldehyde–Fumig–for Aphid.

A.K. Burditt et al., *Journal of Economic Entomology* (1963) 56(3): 261–265, Screening of Fumigents, Fruit Fly.

H.J. Bhambhani, *World Review of Pest Control* (1964) 3: 53–56, Recent Advances in Vacuum Fumigation.

W.B. Brown and S.G. Heuser, *J. Sci. Food Agric.* (1953) 4: 48–57, Behavior of Fumigants During Vac. Fumig.

J. Ferguson and H. Pirie, *Annals of applied Biology* (1948) 35: 532–550, Toxicity of Vapors to Grain Weevil.

A. Kubo et al. *J. Agric. Food Chem.* (1995) 43: 1629–1633, Antimicrobial Act. of Olive Oil Compounds.

H.A.U. Monro et al. *J. Stored Prod. Res.* (1966) 1: 207–222, IInfln. of Vapor Press on Mortality of Prod.

H.A.U. Monro, *Manual of Fumigation for Insect Control* 2nd Ed. (1969) 79: 232–239, Manual Fumigation for Insect.

E.R. Sasscer and L.A. Hawkins, *Bulletin of the U.S. Dept. of Agriculture* (1915) 186: 1–6, Fumigating Seed.

P.L. Sholberg and A.P. Gaunce, *Hort Science* (1995) 30(6): 1271–1275, Fumigation of Fruit w/AA.

P.L. Sholberg, *Plant Disease* (1998) 82(6):689–693, Fumigation of Fruit W/Short Chain Org. Acids.

J.L. Smilanick et al., *Plant Disease* (1994) 78(9): 861–865, Germinability of Tilletia spp. Teliospores.

J.K. Stewart and Y. Aharoni, *J. Amer. Soc. Hort. Sci.* (1983) 108(2): 295–298, Vac. Fumig. w/Ethyl Formate.

B.C. Thornton and W.N. Sullivan, *Journal of Economic Entomology* (1964) 57(6): 852–854, High Vac. on Insect.

S.F. Vaughn et al., *Journal of Food Science* (1993) 58(4): 793–796, Volatile Compounds From Raspberry Fruit.

R. Yonglin et al., *J. Agric. Food Chem.*, (1997) 45(7): 2626, Effect of Grain Fuming on Lipids.

* cited by examiner

*Primary Examiner*—Shelley A. Dodson
*Assistant Examiner*—Alton Pryor
(74) *Attorney, Agent, or Firm*—Townsend and Townsend and Crew LLP

(57) ABSTRACT

Pest infestations of plant materials are controlled by the application of vaporized organic aldehydes of 3 or more carbon atoms, with at least the initial part of the exposure being performed under a subatmospheric pressure.

13 Claims, No Drawings

VOLATILE ALDEHYDES AS PEST CONTROL AGENTS

BACKGROUND OF THE INVENTION

Among the many types of organic compounds that have been used as insecticides, very little attention has been paid to aldehydes. The only aldehyde that has received thorough investigation is acetaldehyde (ethanal). Studies involving acetaldehyde gas are reported by Aharoni, Y., et al., in "Acetaldehyde—a Potential Fumigant for Control of the Green Peach Aphid on Harvested Head Lettuce," *J. Econ. Entomol.* 72(4):493–5 (1979), by Aharoni, Y., et al., in "Thrips Mortality and Strawberry Quality after Vacuum Fumigation with Acetaldehyde or Ethyl Formate," *J. Amer. Hort. Sci.* 105(6):926–929 (1980), and by Stewart, J. K., et al., in "Acetaldehyde Fumigation at Reduced Pressures to Control the Green Peach Aphid on Wrapped and Packed Head Lettuce," *J. Econ. Entomol.* 73(1):148–152 (1980). Various exposure periods were used in these studies, with various reduced pressures in the latter two studies, and the results show activity but no clear trend in data nor statistical difference between treatments at different pressures. The use of acetaldehyde as a commercial fumigant was not pursued further.

Insecticidal studies with aldehydes of three or more carbon atoms are few and inconclusive. Ferguson, J., et al., "The Toxicity of Vapours to the Grain Weevil," *Ann. Appl. Biol.*, 35:532–550 (1948), tested 94 compounds differing widely in structure, four of which were aldehydes, in exposures of five hours at 25° C. and atmospheric pressure. A screening study by Hinman, F. G., "Screening tests of compounds as fumigants for eggs and larvae of the oriental fruit fly," *J. Econ. Entomol.* 47(4):549–556 (1954) covered 189 compounds, one of which was propanal, which was not considered a promising candidate for further study. The same investigator participated in a second screening study, reported by Burditt, A. K., et al., "Screening of Fumigants for Toxicity to Eggs and Larvae of the Oriental Fruit Fly and Mediterranean Fruit Fly," *J. Econ. Entomol.* 56(3):261–265 (1963), where acetaldehyde, butyraldehyde, and isobutyraldehyde were included among 108 compounds screened, without including propanal. Exposure times were two hours at 75° F. (approximately 25° C.) and atmospheric pressure.

No further studies were reported on the use of aldehydes as insecticides, apparently because the low-to-moderate toxicity that the aldehydes demonstrated in these studies rendered them too weak for commercial utility. Furthermore, none of these published studies involved tests performed in the presence of an agricultural crop.

Of further potential relevance to this invention is prior art on applying gaseous fumigants under partial vacuum. An early study was reported by Sasscer, E. R., et al., "A method for fumigating seeds," *U.S.D.A. Bull. No.* 186: 1–6 (1915). The effect of vacuum can vary dramatically, however, with some compounds displaying increased potency under vacuum (Bhambhani, H. J., "Recent advances in vacuum fumigation," *Wld. Rev. Pest Control*, 3:53–56 (1964), others decreased potency (Monro, H. A. U., et al., "The influence of vapor pressure of different fumigants on the mortality of two stored product insects in vacuum fumigation," *J. Stored Prod. Res.* 1:207–222(1966), and still others no difference in potency (Aharoni, Y, et al., 1980, cited above). The advantage of vacuum fumigation as reported by the prior art is its effect in increasing penetration of a pesticide into a dense load (Monro, H. A. U., "Vacuum Fumigation" in *Manual of fumigation for insect control*, 2d edition, FAO, Rome, 1969; and Stewart, J. K., et al., cited above), such as densely packed dates (Brown, W. B. and Heuser, S. G., "Behaviour of fumigants during vacuum fumigation: I. Penetration of methyl bromide into boxes of dates," *J. Sci. Food Agric.* 4:48–57 (1953)), rather than achieving an increase in potency of a pesticide in an otherwise empty container.

SUMMARY OF THE INVENTION

It has now been discovered that organic aldehydes having 3 or more carbon atoms when applied as gaseous fumigants under reduced pressure demonstrate a toxicity to insects that is substantially greater than the same compounds demonstrate at atmospheric pressure. In direct comparison with studies reported in the prior art, the inventors herein have found that lethal doses for the same level of toxicity were one-half to one-fifth when the aldehydes were applied under reduced pressure than when applied at atmospheric pressure.

These and other objects, features, and advantages of the invention will become more apparent from the description that follows.

DETAILED DESCRIPTION OF THE INVENTION AND PREFERRED EMBODIMENTS

The aldehydes used in the practice of this invention are those having three or more carbon atoms, preferably from 3 to 12 carbon atoms, and include straight-chain, branched-chain, saturated, and unsaturated aldehydes, including both monounsaturated and polyunsaturated. More preferred are straight-chain and branched-chain saturated aldehydes having 3 to 10 carbon atoms, straight-chain and branched-chain monounsaturated aldehydes (i.e., those containing a single double bond) having 3 to 10 carbon atoms, and straight-chain and branched-chain diunsaturated aldehydes (i.e., those containing two double bonds) having 3 to 10 carbon atoms. Even more preferred are straight-chain and branched-chain saturated aldehydes having 3 to 7 carbon atoms, and straight-chain and branched-chain monounsaturated aldehydes having 3 to 7 carbon atoms. Specific examples of aldehydes whose use is within the scope of this invention are 1-propanal (1-propionaldehyde), 1-butanal (1-butyraldehyde), isobutanal (isobutyraldehyde), 1-pentanal, 1-hexanal, 1-heptanal, 1-octanal, 1-nonanal, 1-decanal, the 2-monounsaturated analogs of the above, the 2,4-diunsaturated analogs of those having 5 or more carbon atoms, and the 2-, 3- ,4-, 5-, or 6-substituted analogs (and analogs substituted at two or more of these locations) where the substituents are methyl, ethyl, propyl, isopropyl or combinations thereof. Particularly preferred aldehydes are 1-propanal, 1-butanal, 1-pentanal, isobutanal, 2-methylbutanal, 2-methylpentanal, 2-pentenal, 2-methyl-2-butenal, 2-methyl-2-pentenal, and 3-methyl-2-butenal. The aldehydes may be applied either individually or in combination.

In accordance with the invention, the aldehyde or aldehydes are applied to the pest-infested region or crop in vapor form in an atmosphere in which the total pressure surrounding the region or crop is less than 300 mmHg (absolute) (0.4 atmosphere), preferably from about 1 mmHg to about 100 mmHg, more preferably from about 5 mmHg to about 50 mmHg, and most preferably from about 10 mmHg to about 35 mmHg. These pressures are to be understood as the total pressure, which is not necessarily the partial pressure of the vaporized aldehyde, which may constitute either part or all of the total pressure. In most cases, the atmosphere will contain a mixture of the vaporized aldehyde and air or some other gas (such as $CO_2$, for example) that is not harmful to the crop. The total pressure is distinct from the dosage of the aldehyde, which is addressed below.

The duration of exposure to the aldehyde in accordance with this invention will be that amount of time sufficient to achieve control of the insects, i.e., killing of the majority, preferably substantially all, and most preferably all, of the insect population. The exposure at these subatmospheric pressures may constitute the entire duration of the fumigation process or an initial portion of the fumigation process, followed by raising of the pressure to atmospheric pressure. In some cases pest mortality may be increased and damage to the crop decreased by allowing the treatment to continue at atmospheric pressure after prolonged exposure to low pressure. Accordingly, the low-pressure fumigation can be performed in an enclosed vessel under partial vacuum, followed by letting air (or an air/gas mixture such as 50% $CO_2$) in to raise the total pressure to atmospheric. The period of low-pressure exposure may vary depending on the dosage, the type of insect and the degree of infestation. In most cases, best results will be obtained with a low-pressure exposure time of at least about 10 minutes, preferably from about 10 minutes to about 2 hours, and more preferably from about 20 minutes to about 2 hours, and most preferably from about 20% to about 50% of the aldehyde treatment period.

The dosage of aldehyde applied will be any insecticidally effective amount, i.e., any amount that within the exposure time will produce the degree of destruction discussed above. This amount may vary with the choice of aldehyde and the exposure time, and for these reasons is not critical to the invention. Since the application of the aldehyde to the infested crop material will generally be performed in an enclosed vessel to contain the reduced pressure, the dosage is defined herein as the amount by weight of the aldehyde to be vaporized per unit internal volume of the vessel, which is approximately equal to the air space or essentially the total volume inside the vessel, assuming that the volume occupied by the plant material is negligible relative to the internal volume of the vessel. In most cases, best results will be achieved with a dosage within the range of about 1.0 to about 300 mg of aldehyde per liter of gas volume within the vessel. Preferred dosages are about 10.0 to about 200 mg of aldehyde per liter of volume, and more preferred dosages are from about 10.0 to about 100 mg of aldehyde per liter of volume. Optimal dosages will vary in some cases with the amount of plant material contained in the vessel, since the plant material may absorb a significant quantity of the aldehyde, at times as much as approximately 75%.

Pest control may be improved by artificially increasing vapor circulation in the vessel in which the aldehydes are applied. This can be achieved by placing a fan inside the chamber or incorporating some other mixing mechanism. The result may be a reduction in the damage to the plant material as well as an increase in the pesticidal activity of the aldehyde.

The atmospheric temperature at which the aldehyde is applied is not critical to the invention and may vary, although it has been discovered that the effectiveness of the application is greater in some cases at temperatures above about 20° C. Preferred temperatures of application are therefore those in the range of about 10° C. to about 50° C., and most preferably from about 22° C. to about 35° C.

This invention is useful for the control and elimination of a wide variety of insects, arachnids and microorganisms, and particularly agricultural insect and mite pests. Examples are aphids, thrips, mites, whiteflies, fruitflies, houseflies, scales, leafhoppers, caterpillars, cockroaches, beetles, and various fungi and bacteria. Use of the invention for the control of insects is preferred. Effective application can be made to either eggs, larvae, pupae, or adult insects, although application to larvae and adults is preferred.

The crop materials to be protected by this invention include materials from agricultural crops such as food crops for human consumption (such as fruits, vegetables, and grains), crops for animal consumption (such as grains and grasses), crops for use in textile manufacture (such as cotton, flax and hemp), crops for use as construction materials (such as timber and bamboo), and ornamental plants. Application can be made to seeds, seedlings, growing crops, harvested crops, and any parts of the crops either before or after harvesting, such as leaves, stems, fruits or flowering parts. The invention is of particular interest as a post-harvest treatment of crops, including those that are intended for export as well as those that are subject to quarantine regulations.

The following examples are offered for purposes of illustration and are intended neither to limit nor to define the scope of the invention.

EXAMPLE 1

A series of aldehydes within the scope of this invention were tested against aphids at reduced pressure (30 mmHg total pressure, absolute) for thirty minutes followed by atmospheric pressure for 1.5 hours, and separately (for comparison) at atmospheric pressure for two hours. In both cases, the test compounds were applied at 24° C. (±1) by injection into an enclosed tank having an internal volume of 9.5 liters and containing one broccoli leaf infested with about fifty green peach aphids (*Myzus persicae*). Injection was performed by syringe through a septum in the tank, the inner side of the septum shielded by a wire mesh supporting filter paper to eliminate splattering of the test compound. The compound once injected volatilized immediately. The pressure was established by air in the tank before injection of the compound; in experiments where the pressure was initially low and raised to atmospheric level after thirty minutes, the pressure rise was achieved by letting air into the tank without loss of any of the vapors already in the tank. The dosages were varied to determine $LD_{50}$ values (i.e., the minimum doses that resulted in killing 50% of the aphids). Each dose was expressed in milligrams of the test compound per unit volume of the tank (in liters). The results are shown in Table I. The number of replicates for each test was 4–6, except for 1-hexanal and 1-heptanal, for which the figures represent only one replicate.

TABLE I

Comparative Test Results on Aphids $LD_{50}$'s in mg of Test Compound per Liter of Tank Volume

| Test Compound | This invention: 30 mmHg, 0.5 h 760 mmHg, 1.5 h | Prior art: 760 mmHg, 2 h | $LD_{50}$ ratio: prior art ÷ invention |
|---|---|---|---|
| 1-Propanal | 2.1 (±1.0) | 7.3 (±2.6) | 3.5 |
| 1-Butanal | 10.8 (±8.8) | 26.1 (±9.0) | 2.4 |
| Isobutanal | 4.6 (±2.3) | 24.4 (±3.2) | 5.3 |
| 1-Hexanal | <5 | 19.4 | 3.9 |
| 1-Heptanal | 5 | 15 | 3 |

The last column in Table I shows that utilization of the method of the invention (by performing the initial part of the exposure at subatmospheric pressure) resulted in an increase of potency of from about 2 to about 5 times.

EXAMPLE 2

Following a procedure similar to that of Example 1, a series of aldehydes within the scope of this invention were tested against black bean aphids (*Aphis fabae*) at 30 mmHg and separately at 760 mmHg (both representing total pressure, absolute), at various exposure times. The compounds were applied at about 20° C. to filter paper in a small Erlenmeyer flask, and a valve was then opened between the flask and a 3-liter tank (which had been evacuated to 30 mmHg for the lower pressure tests and left at atmospheric pressure for the comparison tests), the 3-liter tank containing one leaf disk floating in a plastic cup of water, and ten target aphids. Mortality of the aphids in terms of the $LD_{90}$ (minimum for kill of 90% of the aphids) was observed and recorded 24 hours after the start of exposure. The results are shown in Table II.

TABLE II

Further Comparative Test Results on Aphids

| Test Compound | Exposure Time (minutes) | $LD_{90}$'s in mg of Test Compound per Liter of Tank Volume | |
|---|---|---|---|
| | | This invention: 30 mmHg | Prior art: 760 mmHg |
| Saturated Aldehydes: | | | |
| 1-Propanal | 20 | 121 | 721 |
| 1-Butanal | 20 | 42 | 971 |
| 1-Pentanal | 20 | 81 | 314 |
| 1-Hexanal | 20 | | 372 |
| 1-Heptanal | 20 | | 306 |
| 1-Nonanal | 60 | | 222 |
| 1-Decanal | 60 | | 252 |
| Monounsaturated Aldehydes: | | | |
| 2-Pentenal | 20 | 14 | 76 |
| 2-Hexenal | 20 | | 87 |
| 2-Heptenal | 60 | | 250 |
| 2-Nonenal | 60 | | 82 |
| 2-Decenal | 60 | | 272 |
| 2-Undecenal | 60 | | 824 |
| 2-Dodecenal | 120 | | 495 |
| Polyunsaturated Aldehydes: | | | |
| 2,4-Hexadienal | 20 | | 100 |
| 2,4-Heptadienal | 20 | | 86 |
| 2,4-Nonadienal | 90 | | 318 |
| 2,4-Decadienal | 90 | | 288 |
| Other Aldehydes: | | | |
| Isobutanal | 20 | 65 | 495 |
| 2-Methylbutanal | 20 | 178 | 234 |
| 2-Methylpentanal | 20 | 215 | 118 |
| 2-Methyl-2-butenal | 60 | 29 | 254 |
| 3-Methyl-2-butenal | 60 | 35 | 169 |
| 2-Methyl-2-pentenal | 20 | 258 | 167 |
| 2-Isopropyl-5-methyl-2-hexenal | 20 | | 205 |
| 2,6-Dimethyl-5-heptenal | 20 | | 496 |

Table II demonstrates that with only two exceptions, the $LD_{90}$ values are much lower in the practice of the invention at various exposure times than in the prior art method of exposure at atmospheric pressure.

In further trials in this study, aphids were exposed to reduced pressure alone, with no exposure to aldehydes, all other conditions being the same as those described above. This was done to determine whether the improvement seen at low pressure was attributable to the low pressure alone. The results showed that at low pressure in the absence of aldehydes, the aphids were temporarily slowed but suffered no mortality. Accordingly, it is concluded that the lethality due to vacuum alone is insignificant except at extraordinarily low pressures (0.05 to 0.03 mmHg, as reported by Thornton, B. C., et al., "Effects of a high vacuum on insect mortality," *J. Econ. Entomol.* 57:852–854 (1964)), or in exposures exceeding 48 hours, as reported by Aharoni, Y., et al., "Use of Reduced Atmospheric Pressure for Control of the Green Peach Aphid on Harvested Head Lettuce," *Hort. Science* 21(3):469–470 (1986).

EXAMPLE 3

Following a procedure similar to that of the previous examples, a series of aldehydes within the scope of this invention were tested against green peach aphids at 30 mmHg absolute total pressure for thirty minutes followed by atmospheric pressure for ninety minutes, all at 24° C. in a 9.5 liter tank containing 1 head of iceberg lettuce (ranging in weight from 500 mg to 1,000 mg) with a small cardboard cylinder containing fifty aphids placed under the third leaf. Mortality was observed and recorded after 24 hours, and the $LD_{50}$ and $LD_{90}$ values are listed in Table III, each value representing three replicates, with the standard error shown. The difference in $LD_{50}$ values between the data in this example and the data in Example 1 can be attributed to the adsorption of the compounds by the lettuce.

TABLE III

Further Test Results on Aphids in the Presence of One head of Iceberg Lettuce

| Test Compounds | Molecular Weight | mg of Test Compound per Liter of Tank Volume | |
|---|---|---|---|
| | | $LD_{50}$ | $LD_{90}$ |
| Saturated Aldehydes: | | | |
| 1-Propanal | 58 | 87.2 ± 19.2 | 124.6 ± 13.9 |
| 1-Butanal | 72 | 130.1 ± 12.4 | 177.5 ± 14.6 |
| 1-Pentanal | 86 | 71.4 ± 13.2 | 115.7 ± 8.9 |
| Monounsaturated Aldehydes: | | | |
| 2-Pentenal | 84 | 13.1 ± 2.4 | 25.8 ± 7.3 |
| 2-Hexenal | 98 | 24.3 ± 0.5 | 54.4 ± 13.0 |
| Other Aldehydes: | | | |
| Isobutanal | 72 | 193.3 ± 11.4 | 224.1 ± 12.6 |
| 2-Methylbutanal | 86 | 135.7 ± 21.7 | 84.4 ± 7.6 |
| 2-Methylpentanal | 100 | 39.9 ± 6.9 | 54.1 ± 4.1 |
| 2-Methyl-2-butenal | 84 | 76.6 ± 22.4 | 123.6 ± 14.1 |
| 3-Methyl-2-butenal | 84 | 73.9 ± 29.8 | 139.1 ± 6.8 |
| 2-Methyl-2-pentenal | 98 | 33.6 ± 14.0 | 85.8 ± 5.7 |

EXAMPLE 4

Using the procedures of Example 1, a series of aldehydes within the scope of the invention were applied to aphids separately at two temperatures—15° C. and 24° C. The results are shown in Table IV.

TABLE IV

Test Results on Aphids at Different Temperatures

| Test Compounds | LD$_{50}$'s in mg of Test Compound per Liter of Tank Volume | |
| --- | --- | --- |
| | 15° C. | 24° C. |
| 1-Propanal | 7.47 | 2.1 (±1.0) |
| 1-Butanal | 31.0 (±7.1) | 10.8 (±7.1) |
| Isobutyraldehyde | 29.3 (±9.9) | 4.6 (±2.3) |

The foregoing is offered primarily for purposes of illustration. Additional examples as well as modifications and variations of the details given above will be readily apparent to those skilled in the art and are intended to be included within the scope of this invention.

What is claimed is:

1. A method for controlling pest infestation on plant material, said method comprising contacting said plant material with a pesticidally effective amount of an organic aldehyde having 3 to 12 carbon atoms in vapor form in an atmosphere not exceeding about 300 mmHg in total pressure.

2. A method in accordance with claim 1 in which said atmosphere is from about 5 mmHg to about 50 mmHg in total pressure.

3. A method in accordance with claim 1 in which said atmosphere is from about 10 mmHg to about 35 mmHg in total pressure.

4. A method in accordance with claim 1 in which said organic aldehyde is a member selected from the group consisting of straight- and branched-chain saturated organic aldehydes of 3 to 10 carbon atoms, straight- and branched-chain monounsaturated organic aldehydes of 3 to 10 carbon atoms, and straight- and branched-chain diunsaturated organic aldehydes of 3 to 10 carbon atoms.

5. A method in accordance with claim 1 in which said organic aldehyde is a member selected from the group consisting of straight- and branched-chain saturated organic aldehydes of 3 to 7 carbon atoms, and straight- and branched-chain monounsaturated organic aldehydes of 3 to 7 carbon atoms.

6. A method in accordance with claim 1 in which said organic aldehyde is a member selected from the group consisting of 1-propanal, 1-butanal, 1-pentanal, isobutanal, 2-methylbutanal, 2-methylpentanal, 2-pentenal, 2-methyl-2-butenal, 2-methyl-2-pentenal, and 3-methyl-2-butenal.

7. A method in accordance with claim 1 in which said pesticidally effective amount is from about 1.0 to about 300 mg of said organic aldehyde per liter of gas volume surrounding said plant material.

8. A method in accordance with claim 1 in which said pesticidally effective amount is from about 10.0 to about 200 mg of said organic aldehyde per liter of gas volume surrounding said plant material.

9. A method in accordance with claim 1 in which said pesticidally effective amount is from about 10.0 to about 100 mg of said organic aldehyde per liter of gas volume surrounding said plant material.

10. A method in accordance with claim 1 in which said method comprises contacting said plant material with said organic aldehyde in vapor form in said atmosphere for an exposure time of from about 20 minutes to about 2 hours.

11. A method in accordance with claim 1 said method comprises contacting said plant material with said organic aldehyde in vapor form in said atmosphere at a temperature of from about 10° C. to about 50° C.

12. A method in accordance with claim 1 in which said method comprises contacting said plant material with said organic aldehyde in vapor form in said atmosphere at a temperature of from about 22° C. to about 35° C.

13. A method in accordance with claim 1 in which said contacting of said plant material with said organic aldehyde in an atmosphere not exceeding about 300 mmHg total pressure constitutes an initial 20% to 50% portion of a treatment period, the remainder of said treatment period comprising contacting said plant material with said organic aldehyde at approximately atmospheric pressure.

* * * * *